United States Patent [19]

Hort

[11] 4,115,458
[45] Sep. 19, 1978

[54] MIXED POLYHALOGENATED-1,4-BUTANEDIOLS

[75] Inventor: Eugene V. Hort, Wayne, N.J.

[73] Assignee: GAF Corporation, New York, N.Y.

[21] Appl. No.: 820,544

[22] Filed: Jul. 29, 1977

Related U.S. Application Data

[63] Continuation-in-part of Ser. No. 679,747, Apr. 23, 1976, abandoned, which is a continuation-in-part of Ser. No. 551,642, Feb. 21, 1975, abandoned, which is a continuation of Ser. No. 295,102, Oct. 5, 1972, abandoned.

[51] Int. Cl.$^2$ .......................... C07C 31/34; C08J 9/00
[52] U.S. Cl. .................................... 568/847; 252/8.1; 252/56 D; 252/56 R; 260/DIG. 24; 560/76; 560/190; 424/343; 424/308; 424/313
[58] Field of Search ........................................ 260/633

[56] References Cited

U.S. PATENT DOCUMENTS

| | | | |
|---|---|---|---|
| 3,054,739 | 9/1962 | Reicheneder et al. | 260/633 X |
| 3,746,726 | 7/1973 | Reicheneder et al. | 260/633 X |

Primary Examiner—Howard T. Mars
Attorney, Agent, or Firm—Walter C. Kehm; Arthur Dresner

[57] ABSTRACT

2-Chloro-2,3,3-tribromo-1,4-butanediol and processes for producing same by reacting dibromobutenediol in a liquid medium with bromine and chlorine.

3 Claims, No Drawings

MIXED POLYHALOGENATED-1,4-BUTANEDIOLS

This is a continuation-in-part of application Ser. No. 679,747 filed Apr. 23, 1976 now abandoned, which is a continuation-in-part of application Ser. No. 551,642, filed Feb. 21, 1975 and now abandoned, which in turn was a continuation of application Ser. No. 295,102, filed Oct. 5, 1972 and also now abandoned.

This invention relates to a novel mixed polyhalogenated diol, and more particularly relates to the compound 2-chloro-2,3,3-tribromo-1,4-butanediol (hereafter CTBBD) and to a method of preparing it.

The aforementioned compound is useful as a valuable intermediate which may be employed in the production of polyesters by reaction with polybasic acids such as adipic, phthalic, maleic, fumaric, chlorendic, or the like, or their halides, esters, nitriles or anhydrides.

Such polyesters contain a relatively high proportion of halogen, such as chlorine and bromine, to which is attributable such properties as flame resistance, biocidal activity, and the like. In addition to the diesters of the instant product with monobasic acids, which diesters are of interest as cutting oils, those polyesters that are liquid are also of interest as cutting oils.

The instant CTBBD compound is a stable polyhalogenated diol having an obviously high halogen content and, in view of the fact that it is stable and non-lachrymatory at ambient and substantially elevated temperatures, it is particularly effective as a flame-proofing ingredient which can be copolymerized in condensation polymers, i.e., polyurethanes.

This compound is also effective as a biocide due to its high halogen content. It is also believed to be superior in applicable properties and uses to diols containing only one halogen species.

It is known that one may prepare 2,2,3,3-tetrachloro-1,4-butanediol (U.S. Pat. No. 3,054,739) as well as 2,2,3,3-tetrabromo-1,4-butanediol, using cuprous chloride in hydrochloric acid as the catalyst (U.S. Pat. No. 3,746,726), but the tetrabromo product prepared by the process of the latter patent has been found to be unstable. Even after being treated by the heat stabilization step of the present process, such tetrabromo butanediol product is still insufficiently stable.

Bromine is more desirable than chlorine for many purposes, such as flame retardance, and it is desirable to add as much bromine as possible without impairing stability. Chlorine is smaller than bromine and hence gives less steric hindrance and therefore adds more rapidly and gives a more stable product.

When butynediol is treated with even a large excess of bromine at relatively lower temperatures and in the absence of catalyst as in the present process, it brominates only to the dibromobutenediol stage. If dibromobutenediol is treated with chlorine, it gives dibromodichlorobutanediol, which contains less than the optimum bromine content for many purposes. In addition, the yield is very poor because a mixture of oxidation products is formed simultaneously. As above mentioned, excess bromine does not react with dibromobutenediol, without added catalysts at temperatures up to about 30° C. But when bromine and chlorine are both employed according to the present process, the predominating reaction is surprisingly addition of one bromine atom and one chlorine atom yielding CTBBD. Concurrently the amount of oxidation byproducts is lowered. The resulting CTBBD is much more stable than the tetrabromo compound at elevated temperatures.

In accordance with the present invention, there is provided the novel compound 2-chloro-2,3,3-tribromo-1,4-butanediol, and processes for producing said compound by reacting dibromobutenediol in a liquid medium with bromine and chlorine as more fully described below.

When dibromobutenediol is treated with bromine and chlorine under the conditions described below, the product is, as stated, CTBBD. The presence of bromine during such chlorination results in the addition of both a bromine atom and a chlorine atom to the dibromobutenediol reactant, but, in the absence of chlorine, bromine will not add to dibromobutenediol under such conditions. This step is advantageously carried out in a solvent so as to minimize oxidative side reactions. The solvent is, preferably, 5–40% concentrated hydrochloric acid, although also usable as solvents are aqueous solutions of group IA and IIA metal halides, such as, e.g. aqueous sodium chloride and magnesium chloride solutions, and the like, which metal halides are less preferred than the corresponding hydrogen halides, especially HCl. It is believed that these solutions function by reversing the equilibrium of the reaction of halogen with water to form halide plus hypohalite, thereby aiding in enhancing the halogen addition reaction mechanism as opposed to oxidative side reactions. Aqueous hydrochloric acid as solvent is employed at the reaction temperature of the present process, which is preferably between about −20° C and +30° C., more preferably about −15° C to +15° C. Side reactions ordinarily can be suppressed by operating at the lower end of each temperature scale; this, however, must be balanced by the longer time required because of the slower halogenation rate at the lower temperatures.

The solvent employed may also dictate the temperature at which the reaction is run, since each solvent system will freeze when the temperature is low enough. The reaction may be carried out in solution or slurry.

The processes of this invention have been found to enable the attainment of yields of up to about 57% of theoretical of the monochlorotribromo product.

The preparation of 2-chloro-2,3,3-tribromo-1,4-butanediol is effected by the bromination and chlorination of 2,3-dibromo-2-butene-1,4-diol, the latter having been prepared, e.g., by the bromination of 1,4-butynediol by methods well known in the art. The process for preparing CTBBD is generally carried out using substantially stoichiometric amounts of dibromobutenediol, bromine, and chlorine. Up to about a 10% excess of chlorine or bromine can also be used with desirably good results, larger amounts being operative, but economically less desirable. The reaction is carried out at a temperature of from about −20° to about +30° C., and preferably from −15° to about +15° C. Although other procedures can be employed, it is preferred that the reaction be carried out by placing the dibromobutendiol and the concentrated hydrochloric acid into a reaction zone, bringing to the desired temperature range, adding about ½ mole of bromine and thereafter holding at said temperature range with stirring while gradually adding about ½ mole of chlorine, per mole of the dibromobutendiol. When all the chlorine has been added, the reaction mixture is stirred briefly, after which air or nitrogen is preferably, but not necessarily passed through to remove any excess chlorine. A stabilizing treatment is then required, according to which the reaction mixture is heated at about 60° to 100° C. for about 10 minutes to an hour. The mixture is thereafter cooled, filtered, washed, and dried. The crude CTBBD may, if desired, be recrystallized from water or aqueous isopropanol or methanol or the like.

If desired, the bromine reactant may be added gradually and/or together with or in admixture with the chlorine.

When dibromobutenediol is chlorinated in the presence of excess bromine according to this invention, both bromine and chlorine are added, giving a product containing more than two atoms of bromine and less than two atoms of chlorine. When one gram-atom of chlorine is added to a mixture of one-mole of dibromobutenediol and one gram-atom or more of bromine, the product on analysis corresponds to CTBBD. There are also formed small amounts of dibromodichloro compound in the monochlorotribromo compound as a result of dichlorination which accompanies chlorobromination to a small extent. More dichlorination will take place if less than equivalent amounts of bromine are used.

The following example is by way of illustration only. All amounts and proportions referred to herein and in the appended claims are by weight unless indicated otherwise.

EXAMPLE I

Into a one liter flask fitted with a gas inlet tube, thermometer, glass and Teflon stirrer (in a ground glass seal), and a dry ice-cooled reflux condenser, there is charged 246g (1.0 mole) of 2,3-dibromo-2-butene-1,4-diol and 400 ml. of aqueous concentrated hydrochloric acid (37-38%). The mixture is stirred over a 15 minute period and there is then added thereto 80g (0.5 mole) of bromine. The resultant red slurry is cooled to −5° C., and over a period of two hours at −5° C. there is added 39g (0.55 mole) chlorine. When all the chlorine has been added, stirring is continued for 30 minutes, then air is sucked through to remove excess chlorine and the bath lowered.

The mixture is heated to about 80° C. and held at 80°-85° C. for 30 minutes. After cooling to 10° C., it is filtered on a sintered glass funnel, washed with 1 liter of cold water and sucked dry.[1]

[1] If not heated before filtering, the product is initially nearly white, but will on standing at ambient temperatures blacken and fume.

Yield: 222.3g of fine pale tan crystals. On recrystallization from one liter of aqueous isopropyl alcohol (using 10g of charcoal to decolorize), a yield of 205.0g (56.8% of theory) of CTBBD, in the form of white crystals, is obtained which is stable at temperatures up to about 100° C. and substantially stable at temperatures up to at least about 150° C.

| Analysis:   | % C  | % H | % Br | % Cl |
|-------------|------|-----|------|------|
| Found:      | 13.4 | 1.7 | 65.5 | 10.3 |
| Calculated: | 13.3 | 1.7 | 66.4 | 9.9  |

This invention has been disclosed with respect to certain preferred embodiments, and it is understood that various modifications and variations thereof will become obvious to those skilled in the art which are intended to be included within the spirit and scope of this application and the scope of the appended claims.

I claim:

1. 2-Chloro-2,3,3-tribromo-1,4-butanediol.

2. A method for preparing the compound as defined in claim 1 comprising reacting 2,3-dibromo-2-butene-1,4-diol with ½ mole each of bromine and chlorine at a temperature between about −20° and 30° C. in an aqueous solution of hydrochloric acid or of a Group IA or IIA metal halide by adding the required amount of the chlorine to said aqueous solution at said temperature and containing said diol after addition of the required amount of the bromine to said solution and then, after completion of the reaction at said temperture, heating the reaction mixture at about 60 to 100° C. for about 10 minutes to 1 hour, cooling the mixture, and separating therefrom the precipitated 2-chloro-2,3,3-tribromo-1,4-butanediol.

3. A method as defined in claim 2 wherein said aqueous solution contains hydrochloric acid.

* * * * *